(12) United States Patent
Naddaka et al.

(10) Patent No.: US 7,745,471 B2
(45) Date of Patent: Jun. 29, 2010

(54) DERIVATIVES OF 1,2-BENZISOXAZOLE-3-METHANE SULFONIC ACID AS NOVEL INTERMEDIATES FOR THE SYNTHESIS OF ZONISAMIDE

(75) Inventors: Vladimir Naddaka, Lod (IL); Eyal Klopfer, Tel Aviv (IL); Shady Saeed, Haifa (IL); Oded Arad, Rechovot (IL); Joseph Kaspi, Givatayim (IL)

(73) Assignee: Chemagis Ltd., Bnei-Brak (IL)

( * ) Notice: Subject to any disclaimer, the term of this patent is extended or adjusted under 35 U.S.C. 154(b) by 1413 days.

(21) Appl. No.: 11/153,402

(22) Filed: Jun. 16, 2005

(65) Prior Publication Data

US 2006/0014814 A1    Jan. 19, 2006

Related U.S. Application Data

(60) Provisional application No. 60/580,360, filed on Jun. 18, 2004, provisional application No. 60/582,086, filed on Jun. 24, 2004, provisional application No. 60/622,009, filed on Oct. 27, 2004.

(51) Int. Cl.
*A61K 31/42* (2006.01)
*C07D 261/20* (2006.01)

(52) U.S. Cl. ...................................... 514/379; 548/241

(58) Field of Classification Search ................. 514/379; 548/241
See application file for complete search history.

(56) References Cited

U.S. PATENT DOCUMENTS

| 4,172,896 A | 10/1979 | Uno et al. |
| 6,841,683 B2 | 1/2005 | Mendelovici et al. |
| 2003/0114682 A1 | 6/2003 | Nidam et al. |
| 2003/0144527 A1 | 7/2003 | Nidam et al. |
| 2004/0138471 A1 | 7/2004 | Mendelovici et al. |
| 2004/0138472 A1 | 7/2004 | Mendelovici et al. |
| 2005/0027126 A1 | 2/2005 | Nidam et al. |
| 2006/0009644 A1 | 1/2006 | Naddaka et al. |
| 2007/0185177 A1 | 8/2007 | Chattopadhyay et al. |

FOREIGN PATENT DOCUMENTS

| WO | WO 03/020708 | 3/2003 |
| WO | WO 03/072552 | 9/2003 |
| WO | WO 2004/063173 A1 * | 7/2004 |
| WO | WO 2005/030738 A1 * | 4/2005 |
| WO | WO 2005/044808 | 5/2005 |

OTHER PUBLICATIONS

Uno et al., Studies on 3-Substituted 1,2-Benzisoxazole Derivatives. VII. Catalytic Reduction of 3-Sulfamoylmethyl-1,2-benzisoxazole and Reactions of the Resulting Products, 1981, Chem. Pharm. Bull., 30(1), 333-335.*
Brittain "Methods for the Characterization of Polymorphs", in: Polymorphism in Pharmaceutical Solids, 95: 228-229, 1999.
Byrn et al. "The Powder Diffraction Method", in: Solid-State Chemistry of Drugs, 2nd Ed., Chap.3: 62-63, 1999.
Chawla et al. "Challenges in Polymorphism of Pharmaceuticals", CRIPS, 5(1): 9-12, 2004.
Guillory "Generation of Polymorphs, Hydrates, Solvates, and Amorphous Solids", in: Polymorphism in Pharmaceutical Solids, 95(Chap. 5): 183-226, 1999.
Newman et al. "Solid-State Analysis of the Acitve Pharmacuetical Ingredient in Drug Products", DDT, Drug Discovery Today, 8(19): 898-905, 2003.

* cited by examiner

*Primary Examiner*—Kamal A Saeed
*Assistant Examiner*—Kristin Bianchi
(74) *Attorney, Agent, or Firm*—Leydig, Voit & Mayer, Ltd.

(57) ABSTRACT

Derivatives of 1,2-benzisoxazole-3-methanesulfonic acid, which are non-hygroscopic and non-hydrated and their use as intermediates from the preparation of zonisamide are disclosed. Further disclosed are processes of preparing zonisamide from these 1,2-benzisoxazole-3-methanesulfonic acid derivatives, processes of preparing exemplary 1,2-benzisoxazole-3-methanesulfonic acid derivatives and crystalline forms of exemplary 2-benzisoxazole-3-methanesulfonic acid derivatives. A novel process of preparing zonisamide is also disclosed.

6 Claims, 7 Drawing Sheets

DERIVATIVES OF 1,2-BENZISOXAZOLE-3-METHANE SULFONIC ACID AS NOVEL INTERMEDIATES FOR THE SYNTHESIS OF ZONISAMIDE

This application claims the benefit of priority from U.S. Provisional Patent Application No. 60/580,360, filed Jun. 18, 2004, from U.S. Provisional Patent Application No. 60/582,086, filed Jun. 24, 2004, and from U.S. Provisional Patent Application No. 60/622,009, filed Oct. 27, 2004, the teachings of which are incorporated herein in its entirety.

FIELD OF THE INVENTION

The present invention relates to the field of chemical synthesis and more particularly to novel intermediates that can be beneficially used in the preparation of zonisamide, to processes of preparing these intermediates and to processes of preparing zonisamide utilizing these intermediates.

BACKGROUND OF THE INVENTION 3-(sulfamoylmethyl)-1,2-benzisoxazole, also named 1,2-benzisoxazole-3-methanesulfonamide and known as zonisamide is an active pharmaceutically agent that exhibits anti-convulsive and anti-neurotoxic activity and is therefore used as an anti-epileptic agent. Zonisamide has the following chemical formula:

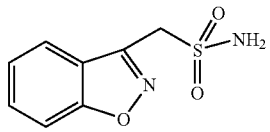

A process of preparing zonisamide was first described in U.S. Pat. No. 4,172,896, to Uno H. et. al. (Dainippon Pharmaceutical Co.). The process taught in this patent is illustrated in Scheme 1 below and is effected by brominating benzioxazole acetic acid (also referred to herein as BIOA) to thereby provide 3-bromomethyl-1,2-benzisoxazole (Compound I); reacting 3-bromomethyl-1,2-benzisoxazole with sodium sulfite in a methanol-water mixture at 50° C., so as to obtain sodium 1,2-benzisoxazole-3-methanesulfonate (Compound II), which is also referred to hereinafter as BIOS-Na; reacting the thus obtained BIOS-Na with a large excess of phosphorus oxychloride so as to obtain 1,2-benzisoxazole-3-methanesulfonyl chloride (Compound III), which is also referred to hereinafter as BIOS-Cl; and reacting the thus obtained BIOS-Cl with gaseous ammonia in ethyl acetate to thereby obtain the zonisamide. The zonisamide is then recrystallized from ethyl acetate.

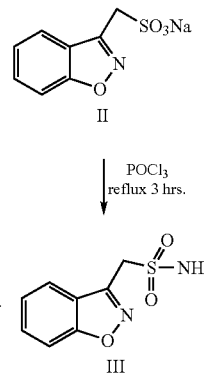

As is demonstrated in the Examples section that follows, while practicing the process taught in U.S. Pat. No. 4,172,896, it was found that the crude intermediate BIOS-Na is obtained by this process as a monohydrate (see, Reference Example 1). While such a hydrated intermediate reacts with the chlorinated agent (e.g., phosphorous oxychloride), the presence of water leads to the formation of hydrogen chloride. Furthermore, since the chlorinating agent reacts with the water, a large access thereof should be used in order to compensate for the loss of reagent that reacts with water. Since both hydrogen chloride and phosphorous oxychloride are considered hazardous, their presence in the reaction waste poses severe environmental problems.

In order to circumvent these limitations, the BIOS-Na monohydrate intermediate must be dried before the chlorination reaction. However, drying BIOS-Na monohydrate in an oven requires a prolonged time period of about 48 hours, whereby the resulting dried BIOS-Na is hygroscopic and thus is difficult to handle and store.

Another process of preparing zonisamide also involves the preparation of BIOS-Na. In this process, BIOS-Na is formed by sulfonating BIOA, with chlorosulfonic acid, to thereby obtain benzioxazole sulfonic acid (also referred to herein as BIOS-H), which is then transformed to BIOS-Na using NaOH. However, such a sulfonation reaction is non-selective and results in a substantial amount of the disulfonated benzioxazole derivative.

WO 03/020708 (by Teva Pharmaceutical Industries Ltd.) teaches various intermediates of zonisamide, processes for their preparation and zonisamide prepared therefrom. Particularly, this patent application teaches the preparation of the sulfonic acid intermediate derivative, BIOS-H, by reacting BIOA with acetic anhydride and sulfuric acid. The BIOS-H is thereafter converted to BIOS-Na. According to the teachings of WO 03/020708, using such a process avoids the formation of the dislufonated product and further avoids the use of chlorosulfonic acid, thus being more environmentally friendly. The preparation of BIOS-Na from BIOA via BIOS-H using the process taught in WO 03/030708 is illustrated in Scheme 2 below.

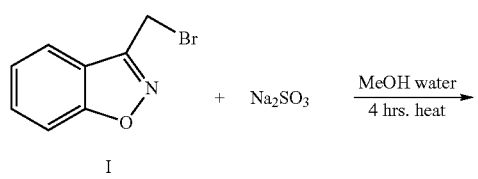

Scheme 1

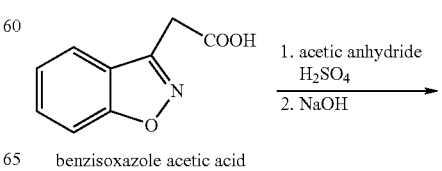

Scheme 2 benzisoxazole acetic acid

-continued

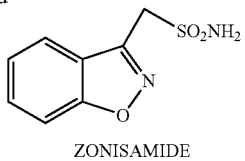

sodium 1,2-benzisoxazole-
3-methanesulfonate (BIOS-Na)

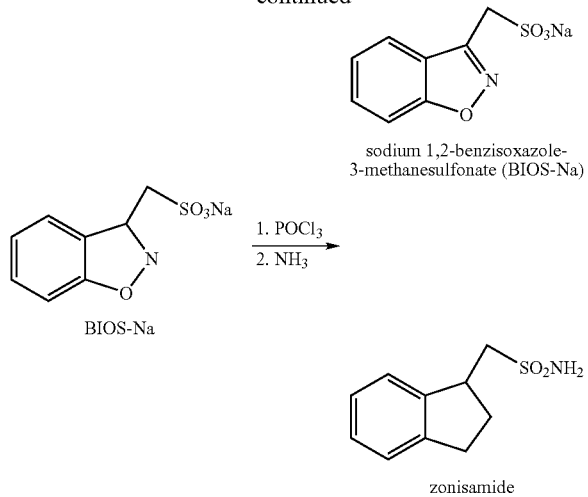

-continued

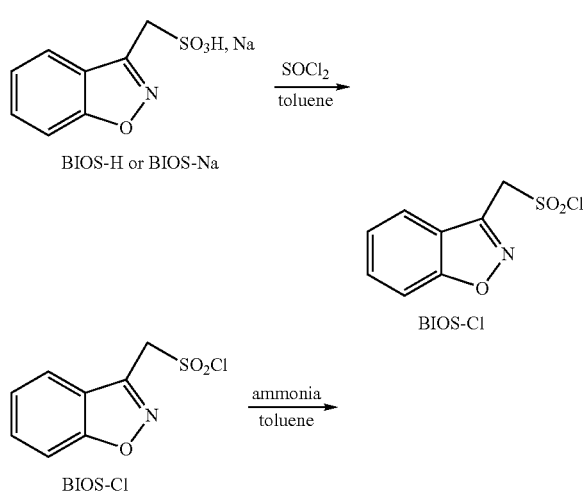

ZONISAMIDE

Thus, the processes taught in the art for preparing BIOS-Na as an intermediate in the synthesis of zonisamide and related compound are limited by the formation of hydrated forms thereof, which either complicates the process as the presence of water requires using a molar excess of the chlorinating agents and involves formation of hydrochloric acid or requires a laborious drying process, whereby the obtained dry intermediate is highly hygroscopic.

In addition, in all of the presently known processes of preparing zonisamide, chlorinating agents such as phosphorus oxychloride, thionyl chloride and phosphorus pentachloride, being some of the most readily available chlorinating agents around the world, are utilized. These chlorinating agents are considered hazardous and in some countries, shipping into and/or ground transportation thereof is restricted. An alternative process of preparing zonisamide, which circumvents the need to use such environmentally unfriendly reagents has not been suggested nor practiced hitherto.

Further according to the teachings of this patent, the preparation of various metallic salts (e.g., sodium, calcium and barium) of BIOS-H is described. These salts are mostly obtained in a hydrated crystalline form thereof, containing between about 1.5 and about 7 weight percentages of water. As is discussed hereinabove, the presence of water in the zonisamide intermediate obtained prior to chlorination, is highly disadvantageous since it requires the use of excess chlorinated agent and involves the production of hydrogen chloride.

WO 03/072552 (to Teva Pharmaceuticals USA, Inc.) describes a process of preparing zonisamide via the intermediate BIOS-Cl. According to the teachings of this patent application, BIOS-Cl is prepared by chlorinating 1,2-benzisoxazole-3-methanesulfonic acid (BIOS-H) or BIOS-Na with thionyl chloride ($SOCl_2$) in an organic solvent. The BIOS-Cl is then reacted with ammonia to thereby obtain zonisamide.

The synthesis of zonisamide from BIOS-H or BIOS-Na via BIOS-Cl, as taught in WO 03/072552 is illustrated in Scheme 3 below.

There is thus a widely recognized need for and it would be highly advantageous to have a novel process of preparing zonisamide and particularly a novel process of preparing intermediates thereof, devoid of the above limitations.

SUMMARY OF THE INVENTION

The present inventors have now surprisingly uncovered that derivatives of 1,2-benzisoxazole-3-methanesulfonic acid, and particularly the ammonium salt and the ester derivatives of 1,2-benzisoxazole-3-methanesulfonic acid, are non-hygroscopic and are typically present in a non-hydrated form and therefore can serve as novel intermediates for the preparation of zonisamide, while circumventing the limitations associated with the presently known processes. The present inventors have further found that zonisamide can be prepared from such derivatives by reaction with equimolar amounts of a chlorinating agent such as oxalyl chloride and have further found that by utilizing such derivatives, zonisamide can be readily obtained in relatively high yield and purity.

According to one aspect of the present invention there is provided a 1,2-benzisoxazole-3-methanesulfonic acid derivative, which is non-hygroscopic and non-hydrated and which can be used as an intermediate for the preparation of zonisamide.

According to further features in preferred embodiments of the invention described below, the 1,2-benzisoxazole-3-methanesulfonic acid derivative is 1,2-benzisoxazole-3-methanesulfonic acid, ammonium salt ($BIOS-NH_4$).

According to still further features in the described preferred embodiments the 1,2-benzisoxazole-3-methanesulfonic acid derivative is a crystalline form of 1,2-benzisoxazole-3-methanesulfonic acid, ammonium salt.

According to still further features in the described preferred embodiments the 1,2-benzisoxazole-3-methanesulfonic acid derivative is a 1,2-benzisoxazole-3-methanesulfonic acid ester.

According to still further features in the described preferred embodiments the 1,2-benzisoxazole-3-methanesulfonic acid ester has the general formula:

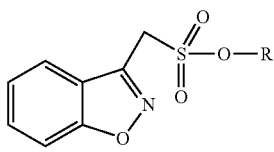

wherein R is selected from the group consisting of alkyl, cycloalkyl, aryl, aralkyl and alkaryl.

According to another aspect of the present invention there is provided a crystalline form of 1,2-benzisoxazole-3-methanesulfonic acid ammonium salt.

According to further features in preferred embodiments of the invention described below, the crystalline form of 1,2-benzisoxazole-3-methanesulfonic acid ammonium salt has a water content lower than 0.5%, preferably lower than 0.1%.

According to still further features in the described preferred embodiments the crystalline form of 1,2-benzisoxazole-3-methanesulfonic acid ammonium salt comprises at least one of the characteristics selected from the group consisting of:

a powder X-ray diffraction pattern exhibiting peaks at diffraction angles 2θ of about 4.8, 9.6, 17.2, 19.3, 24.3, 25.7, 29.5, 29.8, 30.9, 32.6 and 34.2±0.2°, and an infrared spectrum with absorption peaks at about 3184, 3074, 1455, 1194, 1047 and 761 $cm^{-1}$.

According to still further features in the described preferred embodiments the powder X-ray diffraction pattern is substantially as depicted in FIG. 4.

According to still further features in the described preferred embodiments the infrared spectrum has absorption peaks also at about 2924, 2854, 1608, 1515, 1384, 1262, 662 and 579 $cm^{-1}$.

According to still further features in the described preferred embodiments the infrared spectrum is substantially as depicted in FIG. 5.

According to still another aspect of the present invention there is provided a process of preparing 1,2-benzisoxazole-3-methanesulfonic acid ammonium salt, which comprises: providing a first mixture containing 3-bromomethyl-1,2-benzisoxazole and a first alcohol; providing a second mixture containing ammonium sulfite and water; reacting the first mixture and the second mixture to thereby obtain a reaction mixture containing the 1,2-benzisoxazole-3-methanesulfonic acid ammonium salt; and isolating the 1,2-benzisoxazole-3-methanesulfonic acid ammonium salt from the reaction mixture, thereby obtaining the 1,2-benzisoxazole-3-methanesulfonic acid ammonium salt.

According to further features in preferred embodiments of the invention described below, the first alcohol is selected from the group consisting of methanol, ethanol, 1-propanol and 2-propanol.

According to still further features in the described preferred embodiments the isolating is effected by: removing the first alcohol and the water from the reaction mixture, to thereby provide a residue containing the 1,2-benzisoxazole-3-methanesulfonic acid ammonium salt; dissolving the residue in a second alcohol, to thereby provide a solution containing the 1,2-benzisoxazole-3-methanesulfonic acid ammonium salt and optionally insoluble impurities; filtering the insoluble impurities; and removing the second alcohol.

According to still further features in the described preferred embodiments the second alcohol is selected from the group consisting of methanol, ethanol, 1-propanol and 2-propanol.

According to still further features in the described preferred embodiments the 1,2-benzisoxazole-3-methanesulfonic acid ammonium salt is obtained as a crystalline form of 1,2-benzisoxazole-3-methanesulfonic acid ammonium salt.

According to an additional aspect of the present invention there is provided a process of preparing zonisamide, which comprises: providing a fourth mixture containing the 1,2-benzisoxazole-3-methanesulfonic acid derivative of claim 1 and a solvent; providing a fifth mixture containing a chlorinating agent; reacting the fourth mixture and the fifth mixture, to thereby provide a sixth mixture containing 1,2-benzisoxazole-3-methanesulfonyl chloride; reacting the sixth mixture with ammonia, to thereby obtain a reaction mixture containing zonisamide; and isolating the zonisamide from the reaction mixture, thereby obtaining the zonisamide.

According to further features in preferred embodiments of the invention described below, the process further comprises, subsequent to isolating the zonisamide: purifying the zonisamide, to thereby obtain highly pure zonisamide.

According to still further features in the described preferred embodiments the purifying comprises re-crystallizing the zonisamide from an alcohol/water mixture.

According to still further features in the described preferred embodiments the process further comprises, prior to recrystallizing the zonisamide: slurrying the zonisamide in an aqueous solution, to thereby obtain a slurry containing the zonisamide and the aqueous solution; and filtering the zonisamide from the slurry.

According to still further features in the described preferred embodiments the solvent used in the above process is selected from the group consisting of ether, diisopropyl ether, methyl tert-butyl ether, dichloromethane, chloroform, o-xylene, m-xylene, p-xylene, toluene and any mixture thereof.

According to still further features in the described preferred embodiments the process further comprises, prior to reacting the fourth mixture and the fifth mixture: dehydrating the fourth mixture.

According to still further features in the described preferred embodiments the dehydrating comprises azeotropic distillation of the mixture.

According to still further features in the described preferred embodiments the chlorinating agent is selected from the group consisting of phosphorous oxychloride, thionyl chloride, phosphorous pentachloride and oxalyl chloride.

According to still further features in the described preferred embodiments an amount of the chlorinating agent ranges from about 1.0 molar equivalent and about 1.2 molar equivalents relative to the 1,2-benzisoxazole-3-methanesulfonic acid derivative.

According to still further features in the described preferred embodiments the process further comprises, prior to, concomitant with or subsequent to reacting the fourth and fifth mixture: adding to the fourth mixture a reaction facilitator for promoting the reacting.

According to still further features in the described preferred embodiments the reaction facilitator is N,N-dimethylformamide.

According to still further features in the described preferred embodiments the ammonia comprises anhydrous, gaseous ammonia.

According to still further features in the described preferred embodiments the pure zonisamide obtained by this process has a purity that equals to or is greater than 99%, more preferably, that equals to or is greater than 99.85%.

According to still further features in the described preferred embodiments the 1,2-benzisoxazole-3-methanesulfonic acid derivative used in this process is 1,2-benzisoxazole-3-methanesulfonic acid, ammonium salt.

According to still further features in the described preferred embodiments the 1,2-benzisoxazole-3-methanesulfonic acid derivative used in this process is a 1,2-benzisoxazole-3-methanesulfonic acid ester, substantially as described herein.

According to still further features in the described preferred embodiments there is provided zonisamide prepared by the process described above.

According to still an additional aspect of the present invention there is provided a use of the 1,2-benzisoxazole-3-methanesulfonic acid derivative described herein for the preparation of zonisamide.

According to yet an additional aspect of the present invention there is provided a zonisamide having a purity that equals to or is greater than 99%, more preferably, a purity that equals to or is greater than 99.85%.

According to further aspects of the present invention there is provided a process of preparing zonisamide, which comprises: providing a mixture containing a zonisamide intermediate and a solvent; refluxing the mixture while removing water therefrom; and converting the zonisamide intermediate to zonisamide, thereby obtaining the zonisamide.

According to further features in preferred embodiments of the invention described below, the zonisamide intermediate is selected from the group consisting of a salt of 1,2-benzisoxazole-3-methanesulfonic acid, 1,2-benzisoxazole-3-methanesulfonic acid, 1,2-benzisoxazole-3-methanesulfonic acid ammonium salt, 1,2-benzisoxazole-3-methanesulfonic acid ester and 1,2-benzisoxazole-3-methanesulfonyl chloride.

According to still further features in the described preferred embodiments the solvent used in this process is selected from the group consisting of diethyl ether, diisopropyl ether, methyl tert-butyl ether, dichloromethane, chloroform, o-xylene, m-xylene, p-xylene, toluene, DMF and any mixture thereof.

The present invention successfully addresses the shortcomings of the presently known configurations by providing novel derivatives of 1,2-benzisoxazole-3-methanesulfonic acid, which are non-hygroscopic and non-hydrated, and which can be beneficially utilized for the preparation of zonisamide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "mixture" describes a mixture that includes more than one substance and which can be in any form, for example, as a homogenous solution, a suspension, a dispersion, a biphasic solution and more.

As used in this application, the singular form "a", "an" and "the" include plural references unless the context clearly dictates otherwise.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the terms "comprising", "including" and "containing" means that other steps and ingredients that do not affect the final result can be added. These terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
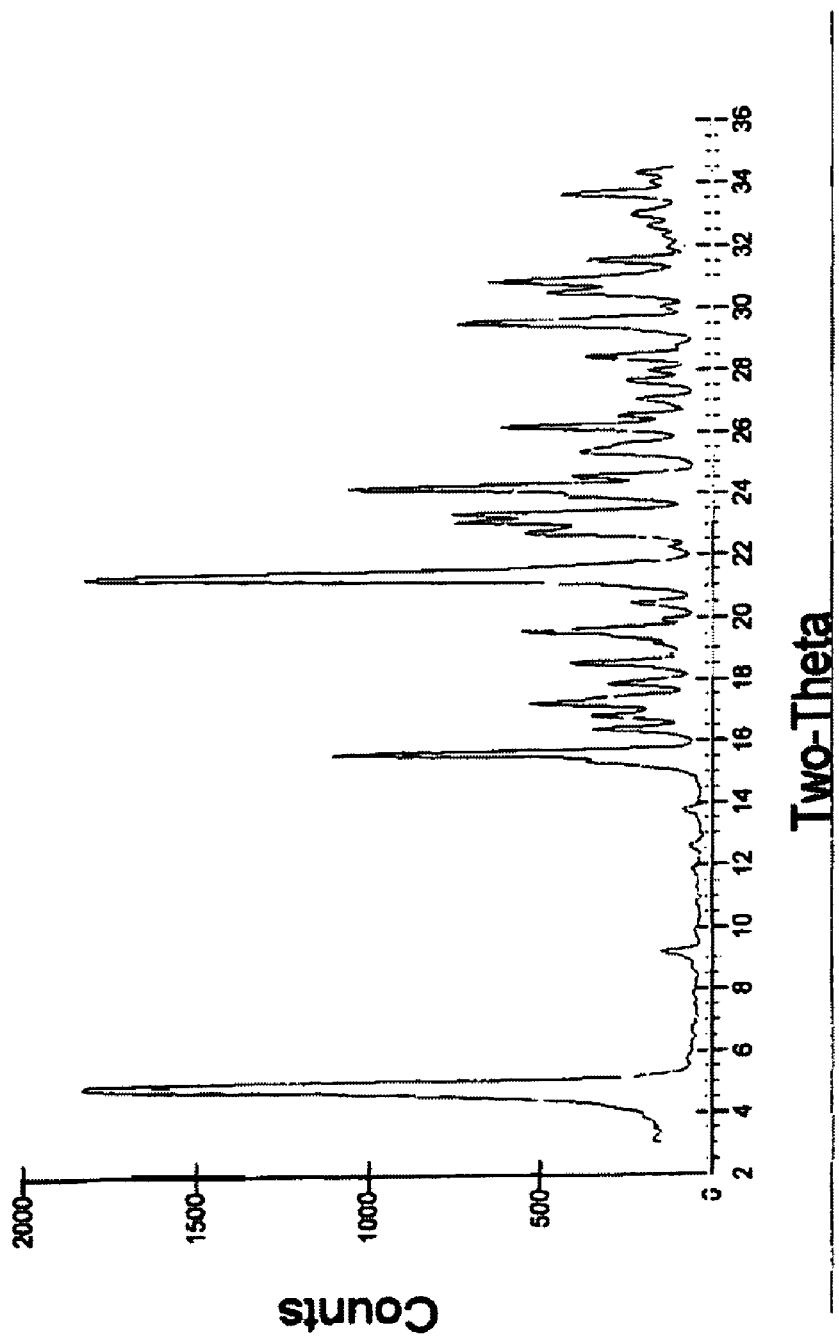
FIG. 1 presents the X-Ray Powder Diffraction (XRD) pattern of BIOS-Na monohydrate, prepared as described in Example 1 of U.S. Pat. No. 4,172,896.

The present invention is of novel derivatives of 1,2-benzisoxazole-3-methanesulfonic acid, which are non-hygroscopic and non-hydrated and which can be efficiently used in the preparation of zonisamide. The present invention is thus further of processes of preparing zonisamide utilizing these 1,2-benzisoxazole-3-methanesulfonic acid derivatives and is further of processes of preparing exemplary derivatives of 1,2-benzisoxazole-3-methanesulfonic acid, and of crystalline forms thereof.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed in detail hereinabove, the presently known processes of preparing zonisamide involve intermediates such as BIOS-Na (Compound II) and related salts of 1,2-benzisoxazole-3-methanesulfonic acid and/or 1,2-benzisoxazole-3-methanesulfonoyl chloride (BIOS-Cl, Compound III). As is further discussed in detail hereinabove, the BIOS-Na, as well as related salts of 1,2-benzisoxazole-3-methanesulfonic acid are hygroscopic and tend to absorb water and are typically obtained in a hydrated form thereof, mostly as a monohydrate form thereof.

As is further discussed hereinabove, using such monohydrates as intermediates for the preparation of zonisamide leads, upon reaction with a chlorinating agent, to the undesired formation of hydrogen chloride and thus requires the use of large excess of the chlorinating agent. While chlorinating agents such phosphorous oxychloride, thionyl chloride and the like are considered relatively hazardous, processes that uses large excess thereof are highly disadvantageous.

In addition, while the monohydrate forms of the BIOS-Na and related intermediates are disadvantageous in the context of preparing zonisamide, the non-hydrated form of BIOS-Na was found to be difficult to obtain, while the resulting dehydrated product was found to be highly hydroscopic, and thus difficult to store and handle. The BIOS-Cl intermediate, which was suggested as an alternative intermediate for the preparation of zonisamide, is also unstable and thus difficult to store and handle.

Since zonisamide is a highly potent pharmaceutically active agent, as described hereinabove, an efficient process for its preparation is highly desired.

In a search for novel intermediates for the preparation of zonisamide, which would be devoid of the limitations cited above, the present inventors have envisioned that derivatives of 1,2-benzisoxazole-3-methanesulfonic acid, other than the known BIOS-Na and related salts of 1,2-benzisoxazole-3-methanesulfonic acid and BIOS-Cl, which are characterized as non-hygroscopic and non-hydrated, could be efficiently used as intermediates for the preparation of zonisamide. As is exemplified in the Examples section that follows, while reducing the present invention to practice, the present invention have uncovered such derivatives of 1,2-benzisoxazole-3-methanesulfonic acid and successfully utilized these derivatives for preparing zonisamide.

Thus, according to one aspect of the present invention there are provided derivatives of 1,2-benzisoxazole-3-methanesulfonic acid, which are characterized as non-hydroscopic and non-hydrated.

As used herein, the term "non-hygroscopic" describes a characteristic of a substance (herein a 1,2-benzisoxazole-3-methanesulfonic acid derivative) by which the tendency of the substance to absorb water is negligible.

The term "non-hydrated" describes a form of the substance which is substantially free of water molecules that are complexed thereto and, in other words, substantially free of a hydrate form thereof. This term is used herein interchangeably with the term "substantially anhydrous".

As used herein, the term "hydrate" describes a complex of variable stoichiometry (e.g., mono-, di-, tri-, tetra-, penta-, hexa-, and so on), which is formed between a substance (herein a 1,2-benzisoxazole-3-methanesulfonic acid derivative) and water molecules.

As is demonstrated in the Examples section that follows, exemplary derivatives of 1,2-benzisoxazole-3-methanesulfonic acid according to preferred embodiments of the present invention were obtained in a non-hydrated form, namely, substantially free of water molecules complexed thereto and were found to have a negligible water content of less than 0.1% (e.g., a water content of about 0.08%).

Thus, according to a preferred embodiment of the present invention, the 1,2-benisoxazole-3-methanesulfonic acid derivatives according to the present invention are further characterized as having a water content lower than 0.5% by weight, more preferably lower than 0.4%, more preferably lower than 0.3%, more preferably lower than 0.2% and even more preferably lower than 0.1% by weight.

As is discussed in detail hereinabove, having such characteristics, and, more particularly, by being non-hygroscopic and stable in a non-hydrated form, the 1,2-benzisoxazole-3-methanesulfonic acid derivatives of the present invention can be efficiently used as intermediates in the preparation of zonisamide.

According to one preferred embodiment of the present invention, the 1,2-benzisoxazole-3-methanesulfonic acid derivative is 1,2-benzisoxazole-3-methanesulfonic acid ester.

Esters of 1,2-benzisoxazole-3-methanesulfonic acid can be readily prepared using known methods. While esters of 1,2-benzisoxazole-3-methanesulfonic acid have been described in the art, the use of these compounds as intermediates in the preparation of zonisamide have not been suggested nor practiced. Furthermore, the advantageous characteristics of these derivatives as intermediates for preparing zonisamide, namely, the non-hygroscopicity and non-hydrated form thereof, have not been taught hitherto.

The relative stability, non-hygroscopicity and non-hydrates form thereof renders such ester derivatives highly suitable for use as intermediates for the preparation of zonisamide, particularly as compared with the BIOS-Na and BIOS-Cl intermediates described in the art.

Preferred esters of 1,2-benzisoxazole-3-methanesulfonic acid according to the present embodiments can be collectively represented by the following general formula:

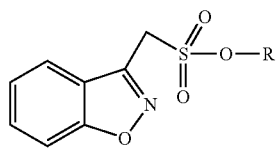

wherein R is selected from the group consisting of alkyl, cycloalkyl, aryl, aralkyl and alkaryl.

As used herein, the term "alkyl" describes to a saturated aliphatic hydrocarbon including straight chain and branched chain groups. Preferably, the alkyl is a lower alkyl having 1 to 4 carbon atoms. The alkyl group may be substituted or unsubstituted.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted.

The term "aryl" describes an all-carbon monocyclic or fused-ring polycyclic (i.e., rings which share adjacent pairs of carbon atoms) groups having a completely conjugated pi-electron system. An aryl group may be substituted or unsubstituted.

The term "alkaryl" describes an alkyl group, as defined herein, which is substituted by one or more aryl groups, as defined herein.

The term "aralkyl" describes an aryl group, as defined herein, that is substituted by one or more alkyl groups, as defined herein.

Preferred ester derivatives of ,2-benzisoxazole-3-methanesulfonic acid according to the present embodiments are those having the general formula above, where R is selected from the group consisting of methyl, ethyl, propyl, isopropyl, butyl, tert-butyl, phenyl, benzyl and the like.

As is demonstrated in the Examples section that follows, an exemplary 1,2-benzisoxazole-3-methanesulfonic acid ester derivative, 1,2-benzisoxazole-3-methanesulfonic acid methyl ester, was beneficially utilized for preparing zonisamide in relatively high yield and purity, while using almost an equimolar amount of a chlorinating agent.

According to another preferred embodiment of the present invention, the 1,2-benzisoxazole-3-methanesulfonic acid derivative is 1,2-benzisoxazole-3-methanesulfonic acid, ammonium salt, which is also referred to herein interchangeably as BIOS-NH$_4$, 1,2-benzisoxazole-3-methanesulfonic acid ammonium salt and an ammonium salt of 1,2-benzisoxazole-3-methanesulfonic acid.

As is demonstrated in the Examples section that follows, BIOS-NH$_4$ is readily obtained by reacting 3-bromomethyl-1,2-benzisoxazole and ammonium sulfite. The obtained BIOS-NH$_4$, although prepared in a water-containing media, is substantially free of water, thus indicating its non-hygroscopicity and its lack of tendency to form hydrates. The obtained BIOS-NH$_4$ has a crystalline structure and is obtained in a single crystalline form, as is detailed hereinbelow.

Based on a known process for preparing ethanesulfonic acid (see, for example, W. Hemilian, *Ann.*, 1873, 168, 145), the present inventors have designed and successfully practiced a novel process of preparing BIOS-NH$_4$.

Thus, further according to the present invention, there is provided a process of preparing 1,2-benzisoxazole-3-methanesulfonic acid ammonium salt. The process, according to this aspect of the present invention, is effected by:
providing a first mixture containing 3-bromomethyl-1,2-benzisoxazole and an alcohol;
providing a second mixture containing ammonium sulfite and water;
reacting, preferably while heating, the first mixture and the second mixture to thereby obtain a reaction mixture containing the 1,2-benzisoxazole-3-methanesulfonic acid ammonium salt; and
isolating the 1,2-benzisoxazole-3-methanesulfonic acid ammonium salt from the reaction mixture.

The above process is illustrated in Scheme 4 below.

Scheme 4

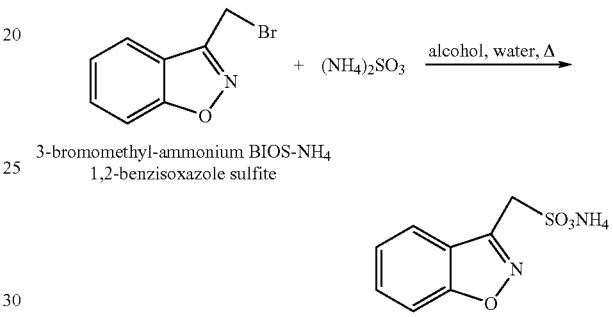

3-bromomethyl-1,2-benzisoxazole   ammonium sulfite   BIOS-NH$_4$

The process according to this aspect of the present invention is therefore effected by reacting an alcoholic solution of 3-bromo-methyl-1,2-benzisoxazole (herein, the first mixture) with an aqueous solution of ammonium sulfite (herein, the second mixture). The reaction media therefore comprises a mixture of alcohol and water.

The ratio between the alcohol and the water may range from about 2:1 to about 1:2 and is preferably 1:1.

The alcohol used in this process (also referred to herein as the "first alcohol") is preferably a lower alcohol such as methanol, ethanol, 1-propanol, 2-propanol, 1-butanol and 2-butanol. More preferably, the alcohol is methanol.

Preferably, more than 1 molar equivalent of (NH$_4$)$_2$SO$_3$ (ammonium sulfite) relative to 3-bromo-methyl-1,2-benzisoxazole is used in this process. More preferably, about 1.75 molar equivalents of (NH$_4$)$_2$SO$_3$ relative to 3-bromo-methyl-1,2-benzisoxazole are used.

As used herein throughout, the term "about" refers to ±10%.

Reacting the first mixture and the second mixture is preferably carried out under heating. More preferably, the reaction is carried out at any temperature from room temperature to 80° C. and more preferably at any temperature from 40° C. to 60° C.

The reaction progress can be easily monitored by high performance liquid chromatography (HPLC). Thus, the reaction may stopped by e.g., cooling the reaction mixture, once a complete disappearance of the starting material 3-bromomethyl-1,2-benzisoxazole is observed.

Once the reaction is completed, and before isolating the obtained BIOS-NH$_4$, the following procedure is preferably performed:

The reaction solvent, namely a mixture of the first alcohol and water, is removed from the reaction mixture under reduced pressure. A second alcohol is then added to the resulting residue and the resulting mixture is heated. Insoluble impurities are then filtered off from the mixture and the second alcohol is removed from the filtrate under reduced pressure, to thereby obtain BIOS-NH$_4$ as a crystalline residue.

The second alcohol used in the above procedure of preparing the crystalline BIOS-NH$_4$ can be the same as the first alcohol or different and is preferably a lower alcohol such as methanol, ethanol, 1-propanol and 2-propanol. More preferably, the second alcohol is methanol.

Further preferably, at least 15 volumes of the alcohol relative to the expected amount of BIOS-NH$_4$ are used in the above procedure of preparing the crystalline BIOS-NH$_4$. More preferably, about 25 volumes of alcohol relative to the expected amount of BIOS-NH$_4$ are used. The expected amount of BIOS-NH$_4$ is typically estimated based on a quantitative reaction yield.

Indeed, as is exemplified in the Examples section that follows, using the process described above, BIOS-NH$_4$ is obtained in almost quantitative yield of about 99%. Being non-hygroscopic, the obtained BIOS-NH$_4$ is dried in an open air.

As is further shown in the Examples section that follows, the BIOS-NH$_4$ obtained by this process has an exceptionally low water content of less than 0.5% and even less than 0.1% and can therefore be efficiently utilized as an intermediate for preparing zonisamide.

In addition to the beneficial characteristics mentioned above, which render BIOS-NH$_4$ a superior intermediate for preparing zonisamide as compared with the presently known intermediates such as BIOS-Na and other salts of 1,2-benzisoxazole-3-methanesulfonic acid, the process of preparing BIOS-NH$_4$, as described hereinabove, is simple to perform, is devoid of laborious and prolonged drying processes, is highly efficient (quantitative) and is highly cost effective. Thus, for example ammonium sulfite is a much cheaper reagent as compared with sodium sulfite that is used for preparing BIOS-Na (see, Scheme 1 above).

As mentioned hereinabove, using the process described above, a single crystalline form of BIOS-NH$_4$ is obtained.

Thus, according to another aspect of the present invention, there is provided a crystalline form of 1,2-benzisoxazole-3-methanesulfonic acid, ammonium salt.

The crystalline form of BIOS-NH$_4$ according to the present embodiments is characterized as having one or more of: (i) a unique powder X-ray diffraction pattern; and (ii) an infrared spectrum with characteristic absorption peaks at about 3184, 3074, 1455, 1194, 1047 and 761 cm$^{-1}$.

Figure 4:
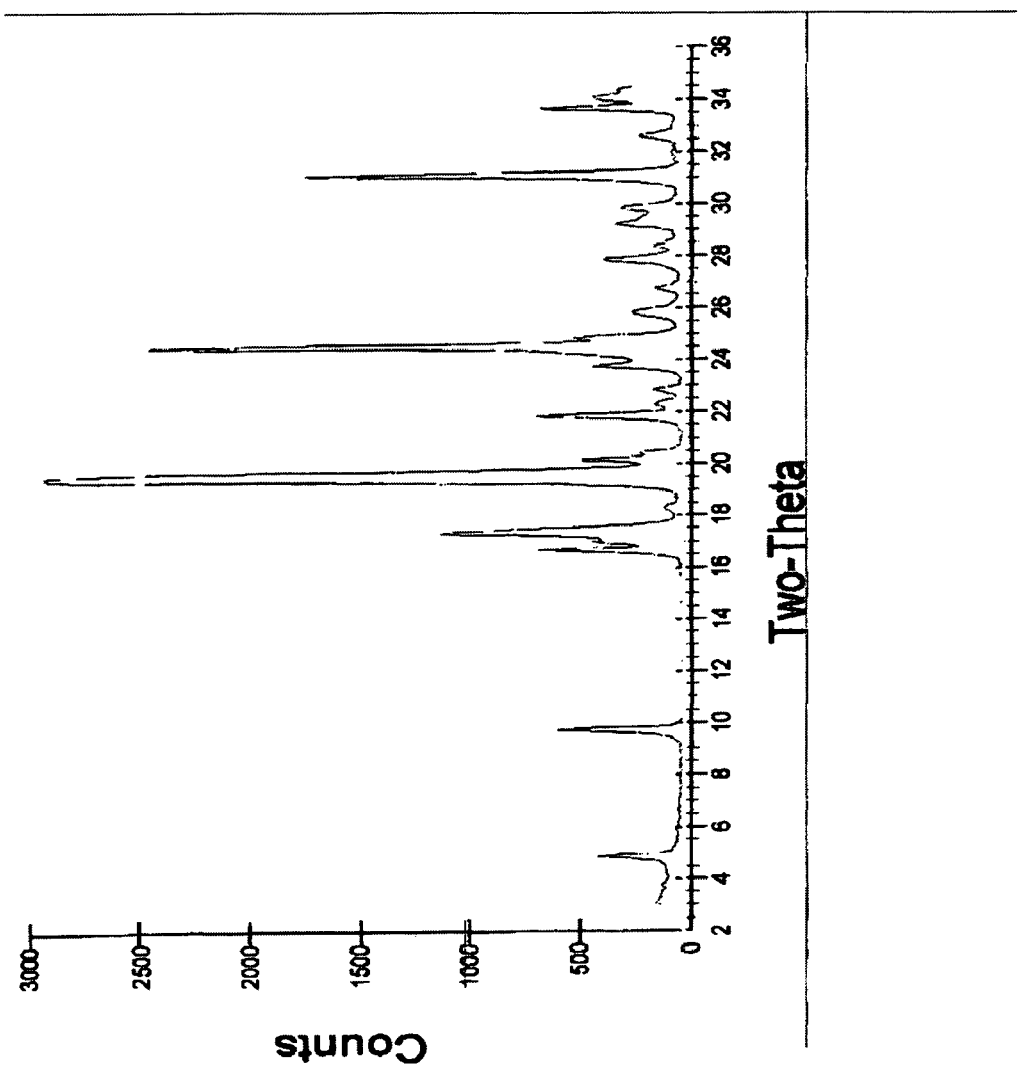
FIG. 4 presents the X-Ray Powder Diffraction (XRD) pattern of a crystalline BIOS-$NH_4$, prepared according to preferred embodiments of the present invention.

The powder X-ray diffraction pattern of the crystalline form of BIOS-NH$_4$ according to the present embodiments is presented in FIG. 4 and exhibits peaks at diffraction angles 2θ of about 4.8, 9.6, 17.2, 19.3, 24.3, 25.7, 29.5, 29.8, 30.9, 32.6 and 34.2±0.2°.

Figure 5:
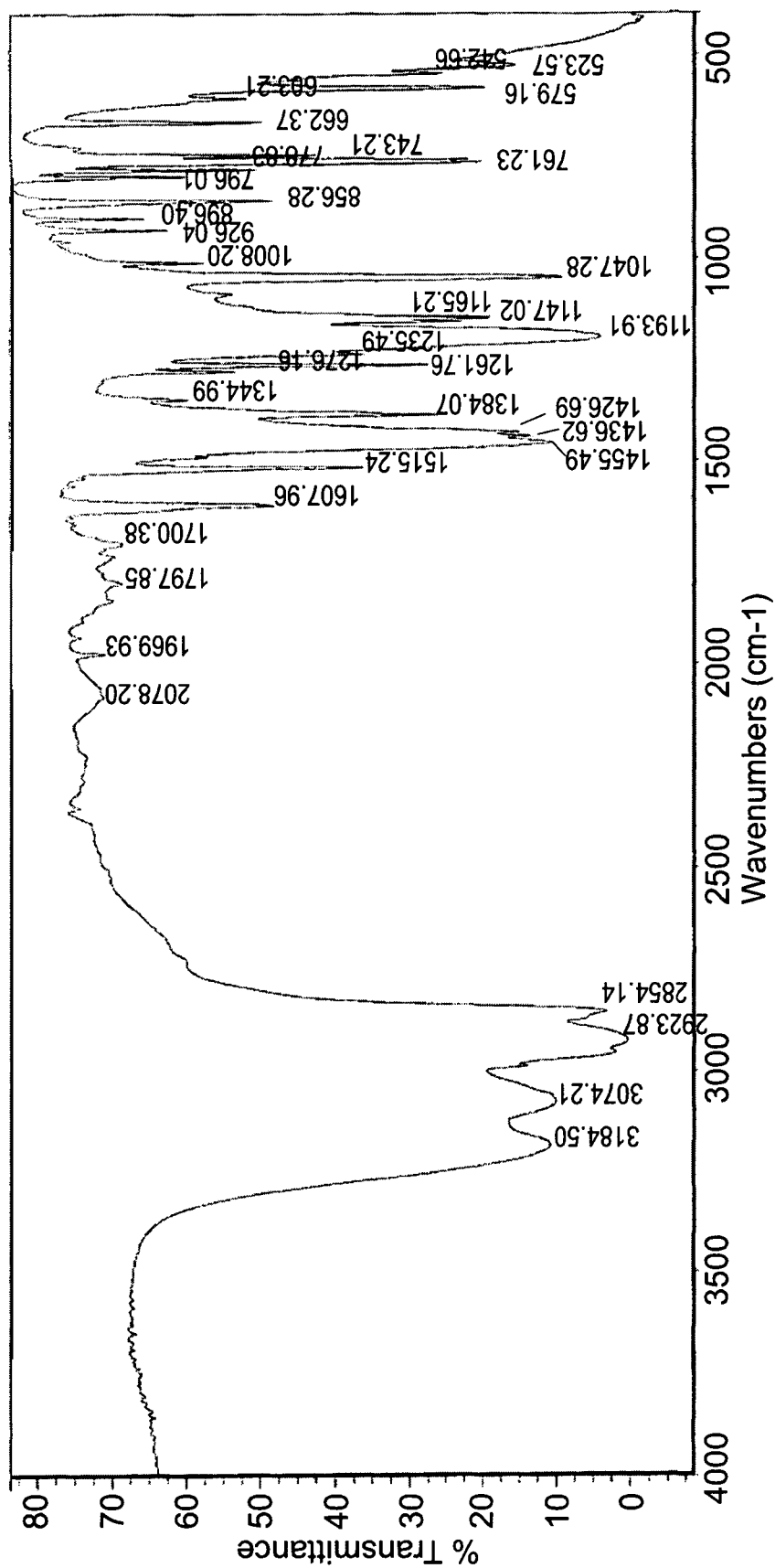
FIG. 5 presents the Fourier Transform Infra-Red Spectroscopy (FTIR) spectrum of a crystalline BIOS-$NH_4$, prepared according to preferred embodiments of the present invention.

The infrared spectrum of the crystalline form of BIOS-NH$_4$ according to the present embodiments is presented in FIG. 5 and has, in addition to the most characteristic absorption peaks delineated above, absorption peaks also at about 2924, 2854, 1608, 1515, 1384, 1262, 662 and 579 cm$^{-1}$.

Figure 6:
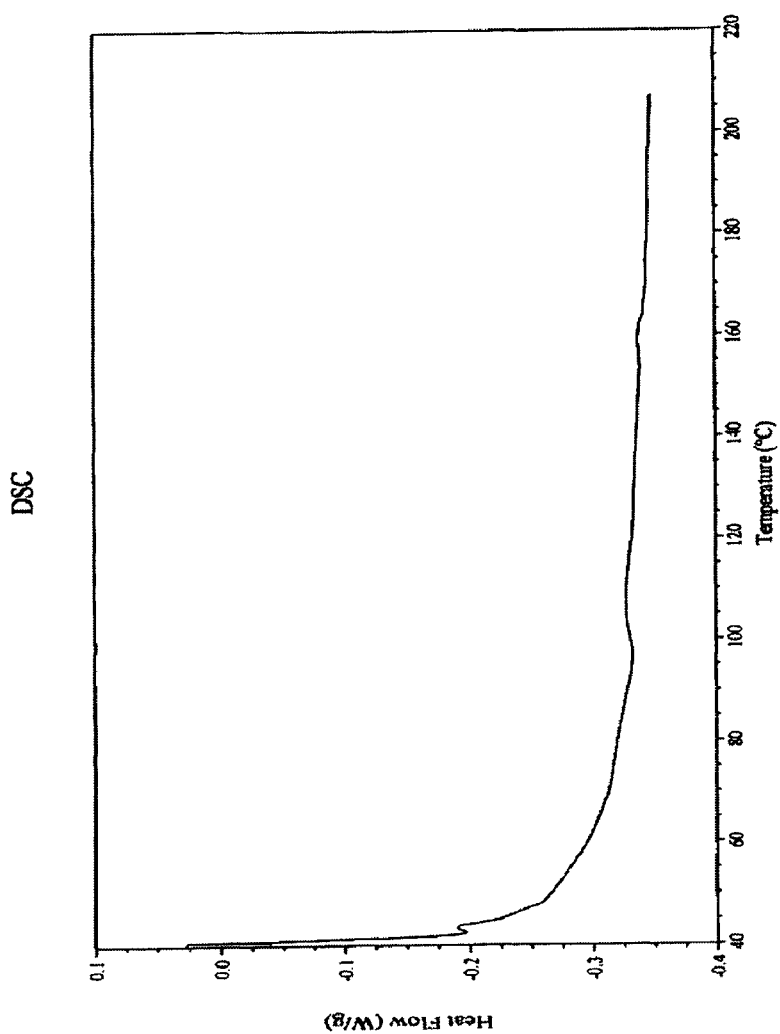
FIG. 6 presents the Differential Scanning Calorimetry (DSC) curve of a crystalline BIOS-NH$_4$, prepared according to preferred embodiments of the present invention.
Figure 7:
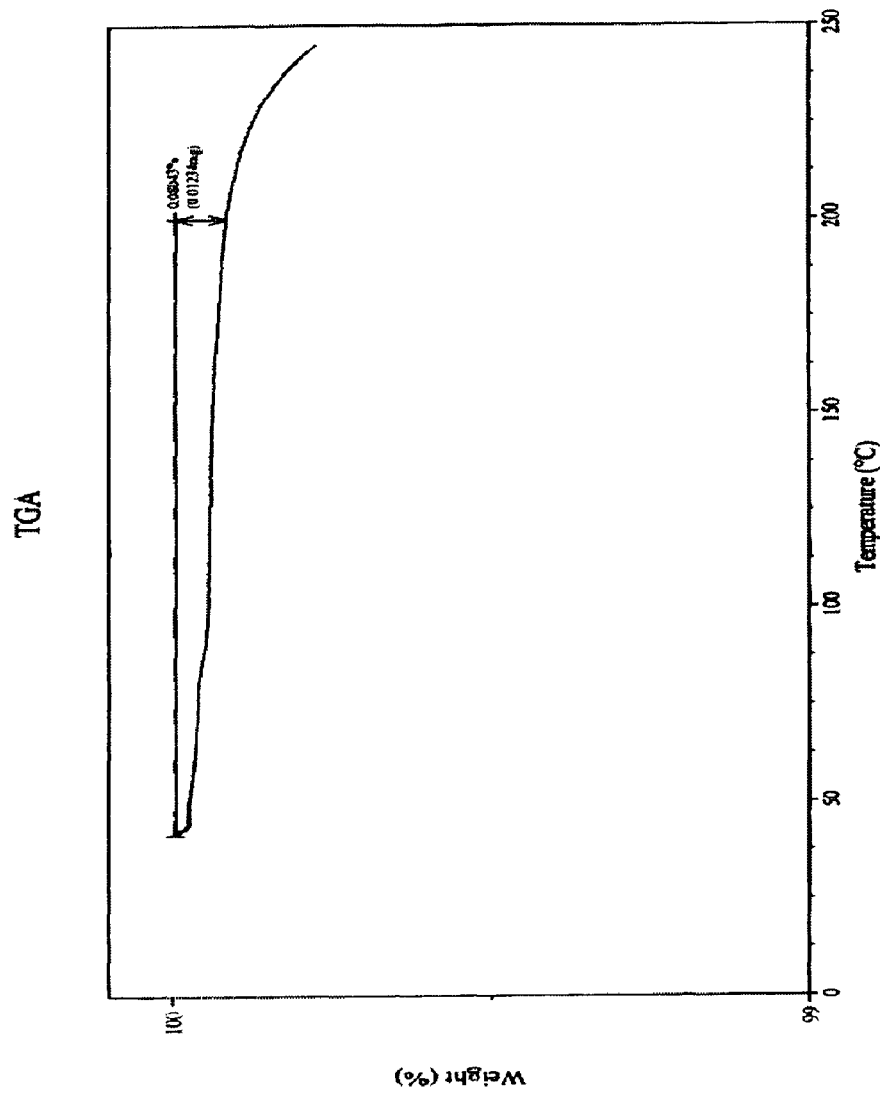
FIG. 7 presents the Thermal Gravimetric Analysis (TGA) thermogram of a crystalline BIOS-NH$_4$, prepared according to preferred embodiments of the present invention.

The DSC profile and the TGA thermogram of the crystalline form of BIOS-NH$_4$ according to the present embodiments are presented in FIGS. 6 and 7, respectively, and clearly show that the compound is substantially free of hydrates and is characterized by extremely low water content of about 0.08%. The low water content of the compound was further confirmed in KF measurements, as is described in detail in the Examples section that follows.

The non-hygroscopic, non-hydrated derivatives of 1,2-benzisoxazole-3-methanesulfonic acid described herein, including any crystalline form thereof, can be efficiently used for preparing zonisamide.

Hence, according to an additional aspect of the present invention there is provided a novel process of preparing zonisamide. The process, according to this aspect of the present invention, is effected by:

providing a mixture containing a non-hygroscopic, non-hydrated 1,2-benzisoxazole-3-methanesulfonic acid derivative as described herein and a solvent (herein, a fourth mixture);

providing a mixture containing a chlorinating agent (herein, a fifth mixture);

reacting the fourth mixture and the fifth mixture, to thereby provide a sixth mixture containing 1,2-benzisoxazole-3-methanesulfonyl chloride (BIOS-Cl, Compound III);

reacting the sixth mixture with ammonia, to thereby obtain a reaction mixture containing zonisamide; and isolating the zonisamide from the reaction mixture.

The process of preparing zonisamide according to this aspect of the present invention is therefore effected by first preparing the intermediate BIOS-Cl (see, Compound III, Scheme 1, and Scheme 3), by chlorinating the 1,2-benzisoxazole-3-methanesulfonic acid derivative and then amidating the BIOS-Cl by means of ammonia. The above process is preferably performed as a one-pot process, while avoiding the isolation of the BIOS-Cl intermediate. Further preferably, the process is performed under inert atmosphere such as nitrogen atmosphere.

The process is preferably performed in an organic solvent (used within the fourth mixture described above) and more preferably in an inert organic solvent.

Non-limiting examples of organic solvents that suitable for use in this context of the present invention include diethyl ether, diisopropyl ether, methyl tert-butyl ether, dichloromethane, chloroform, o-xylene, m-xylene, p-xylene, toluene and any mixture thereof. Preferably, the process is performed in toluene as the solvent.

Preferably, at least 7 volumes of the solvent (relative to the 1,2-benzisoxazole-3-methanesulfonic acid derivative) are used. More preferably, about 10 volumes of the solvent relative to the 1,2-benzisoxazole-3-methanesulfonic acid derivative are used.

As is discussed hereinabove, the process of preparing zonisamide should preferably be carried out under anhydrous conditions, so as to avoid the formation of hydrogen chloride and the use of a large molar excess of a chlorinating agent.

Thus, according to a preferred embodiment, the process according to this aspect of the present invention further comprises, prior to said reacting with said chlorinating agent, drying the fourth mixture. Herein, the terms "drying" and "dehydrating" are used interchangeably and are meant to described a process in which the water content of a mixture and/or a substance is substantially reduced.

The drying is preferably effected in situ, by azeotropic distillation of the fourth mixture containing the 1,2-benzisoxazole-3-methanesulfonic acid derivative and the solvent (e.g., toluene), so as to remove any residual amount of water.

The azeotropic distillation is effected, as is well known in the art, by refluxing the mixture such that an azeotrop of the solvent and water is removed therefrom.

As used herein, the phrase "refluxing a mixture while removing water therefrom" in meant to describe an azeotropic distillation of the mixture, in which the water are removed from the mixture as an azeotrop of water and the solvent.

As is well known in the art, an "azeotrop" refers to a constant boiling mixture of two or more substances that behaves like a single substance, at least during a period of a distillation process in which the two substances are present in a mixture. Thus, an azeotrope exhibits either a maximum, or minimum boiling point compared to the boiling point of one of the substances.

Similarly, as used herein, the phrase "azeotropic distillation" describes a distillation procedure in which an azeotrop is removed from a mixture. As is well-recognized in the art, this phrase is commonly used to describe a distillation procedure in which an azeotrop of water and a non-aqueous, organic solvent is distilled our of a mixture.

Preferably, drying the fourth mixture described above is carried out during at least than 1 hour. More preferably, the drying is carried out during about 2 hours.

The chlorinating agent used in this process according to the present invention can be selected from, for example, phosphorus oxychloride, thionyl chloride, phosphorous pentachloride and oxalyl chloride. However, due to the limitations associated with the use, transportation and storage of chlorinating agents such as phosphorus oxychloride, thionyl chloride and phosphorous pentachloride, described above, the process is preferably effected while using oxalyl chloride as the chlorinating agent.

Hence, according to a preferred embodiment of the present invention, the chlorinating agent used in the process of preparing zonisamide is oxalyl chloride.

Since the intermediate used in this process is a non-hygroscopic, non-hydrated derivative of 1,2-benzisoxazole-3-methanesulfonic acid, the need to use a molar excess of the chlorinating agent is circumvented. Thus, according to a preferred embodiment of the present invention, at least 1 molar equivalent and no more than 1.2 molar equivalents of a chlorinating agent, relative to the 1,2-benzisoxazole-3-methanesulfonic acid derivative, is used. Preferably, between 1.02 and 1.1 molar equivalents of the chlorinating agents are used.

As is discussed above, the use of nearly equimolar amounts of a chlorinating agent renders the process described herein highly advantageous as compared with the prior art processes, which typically utilize about 3 molequivalents of the chlorinating agents relative to the zonisamide intermediate.

The chlorination reaction is preferably performed is the presence of a reaction facilitator. As used herein, the phrase "reaction facilitator" refers to a substance that promotes and/or facilitates a chemical reaction.

An organic amide is traditionally used as a reaction facilitator in such chlorination reactions. Thus, according to a preferred embodiment of the present invention, the reaction facilitator is an organic amide. The organic amide can be selected from, for example, N,N-dimethylacetamide, N-methylpyrrolidone and N,N-dimethylformamide, and preferably is N,N-dimethylformamide (DMF).

Preferably, at least 0.01 molar equivalent of the organic amide relative to the 1,2-benzisoxazole-3-methanesulfonic acid derivative is used. More preferably, about 0.1 molar equivalent of the organic amide relative to the 1,2-benzisoxazole-3-methanesulfonic acid derivative is used.

The organic amide can be added to the fifth mixture, which contains the chlorinating agent, or, alternatively, can be added separately to the fourth mixture, prior to, concomitant with or subsequent to the reacting of the fourth mixture with the fifth mixture.

In a preferred embodiment, the fourth mixture containing the 1,2-benzisoxazole-3-methanesulfonic acid derivative and the solvent is cooled prior to reacting with the fifth mixture. Preferably, the fourth mixture is cooled to about 10° C. The organic amide (e.g., DMF) is then added to the cooled mixture, followed by dropwise addition of the chlorinating agent (e.g., oxalyl chloride). Preferably, the chlorinating agent is added during about 1 hour, while the temperature of the reaction mixture is maintained less than 20° C.

Thus, reacting the fourth mixture and the fifth mixture is typically carried out by slowly adding the chlorinating agent, at relatively low temperature. Once the addition of the chlorinating agent is completed, the resulting reaction mixture (herein the sixth mixture) is preferably heated.

Preferably, the reaction mixture is heated to 40° C.

Further preferably, heating the reaction mixture is carried out during at least 1 hour. More preferably, heating the reaction mixture is carried out during about 2 hours.

Under these conditions, BIOS-Cl is obtained in a nearly quantitative yield, as determined by HPLC (by analyzing a sample withdrawn from the reaction mixture).

As described hereinabove, the thus obtained sixth mixture, which contains the BIOS-Cl intermediate is directly reacted, without further manipulations, with ammonia.

Thus, once the reaction between the fourth mixture and the fifth mixture is completed, the obtained sixth mixture is reacted, in an amidation reaction, with ammonia.

The ammonia used in the amidation reaction can be, for example, anhydrous, gaseous ammonia, aqueous ammonia or "masked ammonia".

When aqueous ammonia is used, the amidation reaction is carried out in a biphasic system, which contains an aqueous phase that includes the aqueous ammonia and a water-immiscible solvent phase such as toluene.

When "masked ammonia" is used in the amidation reaction, the ammonia can be provided as, for example, an ammonium salt including ammonium carbonate, ammonium acetate, and ammonium formate.

Preferably, the amidation reaction is carried out with gaseous ammonia, which is bubbled into the reaction mixture (the sixth mixture described above). The gaseous ammonia can be anhydrous or non-anhydrous, with anhydrous ammonia being preferred.

When gaseous ammonia is used, the reaction mixture is preferably cooled prior to the addition of the ammonia, preferably to about 10° C.

During the reaction with the gaseous ammonia, the reaction mixture is preferably maintained at a temperature that ranges from about 0° C. to about of 30° C., more preferably from about 10° C. to about 18° C.

Preferably, at least 2.5 molar equivalents of ammonia gas relative to the expected amount of BIOS-Cl, calculated based on a quantitative yield, are used in the amidation reaction More preferably, about 4 molar equivalents of ammonia gas relative to expected amount of BIOS-Cl are used.

Further preferably, the gaseous ammonia is bubbled into the reaction mixture during at least 1 hour, more preferably, during about 2 hours.

Once the amidation reaction is completed, the obtained zonisamide is isolated from the reaction mixture. The zonisamide is typically obtained as a colorless precipitate and is preferably isolated from the reaction mixture by filtration.

Using the process described herein, zonisamide is obtained in a relatively high yield greater than 80%. Depending on the 1,2-benzisoxazole-3-methanesulfonic acid derivative used, zonisamide can be obtained in higher yields.

Thus, when BIOS-$NH_4$ is used as the 1,2-benzisoxazole-3-methanesulfonic acid derivative in the process described herein, zonisamide is obtained in a yield greater than 90% and even greater than 93%.

The zonisamide prepared by the process described herein is also characterized by relatively high purity of at least 98% and in some cases of at least 99%, as determined by HPLC. The zonisamide contains no more than 1.5% and preferably no more than 1% of the 1,2-benzisoxazole-3-methanesulfonic acid derivative used, as determined by HPLC.

The thus obtained zonisamide can be further purified, so as to provide highly pure zonisamide.

The purification can be effected by any of the known purification methods, including, without limitation, extraction, column chromatography, preparative low-pressure liquid chromatography, preparative high-pressure liquid chromatography, re-crystallization, slurrying and any combination thereof.

According to a preferred embodiment of this aspect of the present invention, the zonisamide is purified by slurrying and/or recrystallization, as is detailed hereinunder. Preferably, the zonisamide is purified by slurrying and re-crystallization.

The slurrying is preferably effected by providing a slurry containing zonisamide and an aqueous solution. The aqueous solution can water. Optionally and preferably, the aqueous solution further comprises an inorganic base.

The inorganic base can be, for example, ammonium hydroxide, sodium hydroxide, potassium hydroxide and the like, and is preferably ammonium hydroxide.

A solution containing at least 5% ammonium hydroxide, more preferably at least 10%, more preferably at least 20%, and most preferably 25% ammonium hydroxide is used in the slurrying procedure.

At least 2 ml of the aqueous solution relative to 1 gram of solid zonisamide are preferably used in the slurrying procedure. More preferably, about 5.5 ml of the aqueous solution relative to 1 gram of the crude zonisamide are used.

The slurrying process is preferably carried out at ambient temperature, during at least 1 hour and more preferably during 2 hours.

The zonisamide is thereafter filtered from the slurry.

Recrystallizing the zonisamide is effected using known procedures, preferably using an alcohol/water mixture.

The ratio between the alcohol and the water in the mixture preferably ranges from 10:1 to 1:10. In a preferred embodiment, the ratio is about 1:7 alcohol:water.

The alcohol used in the recrystallization procedure is preferably a lower alcohol, such as, for example, methanol, ethanol, 1-propanol, 2-propanol and the like.

Using the above purification procedure and the above process, highly pure zonisamide is obtained. As is exemplified in the Examples section that follows, zonisamide having a purity that equals to or is greater than 99% and even that equals to or is greater than 99.85%, as determined by HPLC, can be obtained.

The highly pure zonisamide is obtained in an overall yield greater than about 60%. Depending on the 1,2-benzisoxazole-3-methanesulfonic acid derivative used, zonisamide can be obtained in higher overall yields.

Thus, when BIOS-NH$_4$ is used as the 1,2-benzisoxazole-3-methanesulfonic acid derivative in the process described herein, highly pure zonisamide is obtained in an overall yield greater than 80%.

Hence, according to another aspect of the present invention there is provided highly pure zonisamide, which has a purity of at least 99% and even of at least 99.85%, as determined by HPLC.

In summary, provided herein are derivatives of 1,2-benzisoxazole-3-methanesulfonic acid, which can be efficiently used as intermediates for preparing zonisamide. These novel intermediates are non-hydroscopic and non-hydrated and are therefore easy to prepare, store, transport and handle. Using these novel intermediates, the use of a molar excess of a chlorinating agent is avoided and zonisamide is obtained in high yield and purity.

The process described herein for preparing zonisamide utilizes the non-hygroscopic, non-hydrated 1,2-benzisoxazole-3-methanesulfonic acid derivatives described herein. As mentioned hereinabove, this process may further include a procedure for removing any residual amount of water that could possibly be present in the reacting solution (e.g., the fourth solution described above). This procedure is highly efficient since it enables the in situ dehydration of the reacting solution and thus circumvents the need to dry the intermediate used in the process and the reaction solvent prior to the reaction.

Such a process can thus be advantageously utilized for preparing zonisamide from any suitable intermediate thereof, including such intermediates that are not necessarily non-hygroscopic and/or non-hydrated.

Thus, according to an additional aspect of the present invention there is provided another process of preparing zonisamide, which is effected by:

providing a mixture of a zonisamide intermediate and a solvent;

refluxing the mixture while removing water therefrom, thus dehydrating the mixture including the zonisamide intermediate and the solvent, by means of azeotropic distillation, as is described in detail hereinabove, so as to provide a mixture containing a dehydrated zonisamide intermediate; and converting the dehydrated zonisamide intermediate to zonisamide.

The process according to this aspect of the present invention can be applied with any suitable intermediate of zonisamide, including, for example, BIOS-Na and any crystalline form thereof, and other salts of 1,2-benzisoxazole-3-methanesulfonic acid (e.g., BIOS-Ba, BIOS-Ca and the like, as described, for example, in WO 03/020708, which is incorporated by reference as if fully set forth herein) and any crystalline form thereof.

As discussed in detail hereinabove, BIOS-Na, the presently most common intermediate for the preparation of zonisamide, is typically obtained as a monohydrate, whereby the presently known methods for its dehydration require prolonged time periods, and high energy. Various crystalline forms thereof, which are taught, for example, in WO 03/020708, in U.S. Provisional Patent Application No. 60/582,086, and in a U.S. patent application entitled "novel crystalline forms of sodium 1,2-benzioxazole-3-methanesulfonate, processes of preparing same and use thereof in the synthesis of zonisamide", the content of which is incorporated herein in its entirety, may also include certain amounts of water. Other salts of 1,2-benzisoxazole-3-methanesulfonic acid are also reported to include water.

Using the process according to this aspect of the present invention enables to obtain zonisamide from such hydrated 1,2-benzisoxazole-3-methanesulfonic acid salts such as BIOS-Na, while using these salts as is, without the laborious dehydration thereof.

Other zonisamide intermediates can be beneficially used for preparing zonisamide according to this aspect of the present invention include, for example, BIOS-Cl (using the process described, for example, in WO 03/072552, which is incorporated by reference as if fully set forth herein) and BIOS-H.

Converting the dehydrated intermediate to zonisamide can be effected by using any of the known procedures, depending on the selected zonisamide intermediate.

Thus, for example, in cases where the intermediate is a salt of 1,2-benzisoxazole-3-methanesulfonic acid (e.g., BIOS-Na, BIOS-Ca, BIOS-Ba or BIOS-NH$_4$) or a 1,2-benzisoxazole-3-methanesulfonic acid ester, converting the intermediate to zonisamide can be effected by reacting the mixture with a chlorinating agent, so as to provide BIOS-Cl; reacting the BIOS-Cl with ammonia, so as to provide zonisamide; and isolating the zonisamide. Preferred features of such a conversion are described hereinabove.

The solvent used in the process according to this aspect of the present invention can be, for example, a non-polar solvent such as o-xylene, m-xylene, p-xylene, toluene, diethyl ether, diisopropyl ether, methyl tert-butyl ether, dichloromethane, chloroform, and any mixture thereof; a polar solvent such as DMF, N-methyl pyrrolidone and N,N-dimethylacetamide, and any mixture thereof; or a mixture of a polar solvent and a non-polar solvent.

Preferably, the solvent comprises toluene. Further preferably, the solvent comprises a mixture of toluene and DMF.

Adding DMF to the mixture containing the intermediate is particularly beneficial since, as described above, DMF can be used as a reaction facilitator in the chlorination reaction. Thus, adding DMF to the mixture containing the intermediate is advantageous since (i) DMF is thus dehydrated in situ and its dehydration prior to addition to the reaction mixture is avoided; and (ii) the addition of DMF at a later stage of the process is circumvented.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

Powder X-ray diffraction patterns were acquired using a Philips PW 1050-70 X-ray Diffractometer. System description: $K_\alpha$=1.54178 Å, voltage 40 kV, current 28 mA, diversion slit=1°, receiving slit=0.2 mm scattering slit=1° with a Graphite monochromator. Experiment parameters: pattern measured between 2θ=4° and 2θ=30° with 0.05° increments; count time 0.5 second per increment. The accuracy of the diffraction angles determined is approximately ±0.2 °2θ.

Infrared (IR) spectra were acquired using a Nicolet™ Avatar™ 360 Fourier-transform Infra-Red Spectrometer with Omnic software version 5.2. All samples were run as Nujol® mulls held between NaCl plates. The accuracy of the wave numbers $v_{max}$ determined is approximately ±4 cm$^{-1}$.

Differential scanning calorimetry (DSC) graphs were recorded using a TA Instruments Q1000 Thermal Analyzer with Universal software (version 3.88). Samples were analyzed inside crimped 40 μl Aluminum pans at a heating rate of 5° C./min.

Thermogravimetric analysis (TGA) was performed using a TA Instruments Q500 Thermal Analyzer with Universal Software (version 3.88). Samples were analyzed inside platinum baskets at heating rate of 5° C./minute.

Water content was measured using a Karl Fischer Titrator (Mettler Toledo Model DL-53) according to standard procedures.

HPLC measurements were performed using HPLC JASCO, LC-1500 series, equipped with Inertsil ODS-2, 5 μm, 4.6×25 cm column, and a UV detector operated on 238 nm. Analyses were performed using the following mobile phase: 0.08 M tetrabutylammonium hydroxide buffer at pH 8.0 with $H_3PO_4$ (70%), acetonitrile (25%) and methanol (5%), at a flow rate of 1.0 ml/minute.

Reference Example 1

Preparation of BIOS-Na Monohydrate According to Example 1 in U.S. Pat. No. 4,172,896

A solution of sodium sulfite (24.3 grams) in water (390 ml) was added to a solution of 3-bromomethyl-1,2-benzioxazole (24 grams) in methanol (390 ml). The mixture was heated, while stirring, at 50° C. for 4 hours and was thereafter concentrated under reduced pressure. The obtained solid residue was dissolved in methanol (750 ml) While warming to 50-60° C. and the insoluble material was filtered off. The filtrate was concentrated under reduced pressure and the residue was washed with diethyl ether to yield crude sodium 1,2-benzioxazole-3-methanesulfonate (18 grams).

The water content of the obtained product, as measured by Karl Fischer (KF) method, was about 7%. This water content corresponds to the water content of a monohydrate form of the compound.

FIG. 1 presents the X-Ray Powder Diffraction (XRD) pattern obtained for the BIOS-Na prepared as above.

Figure 2:
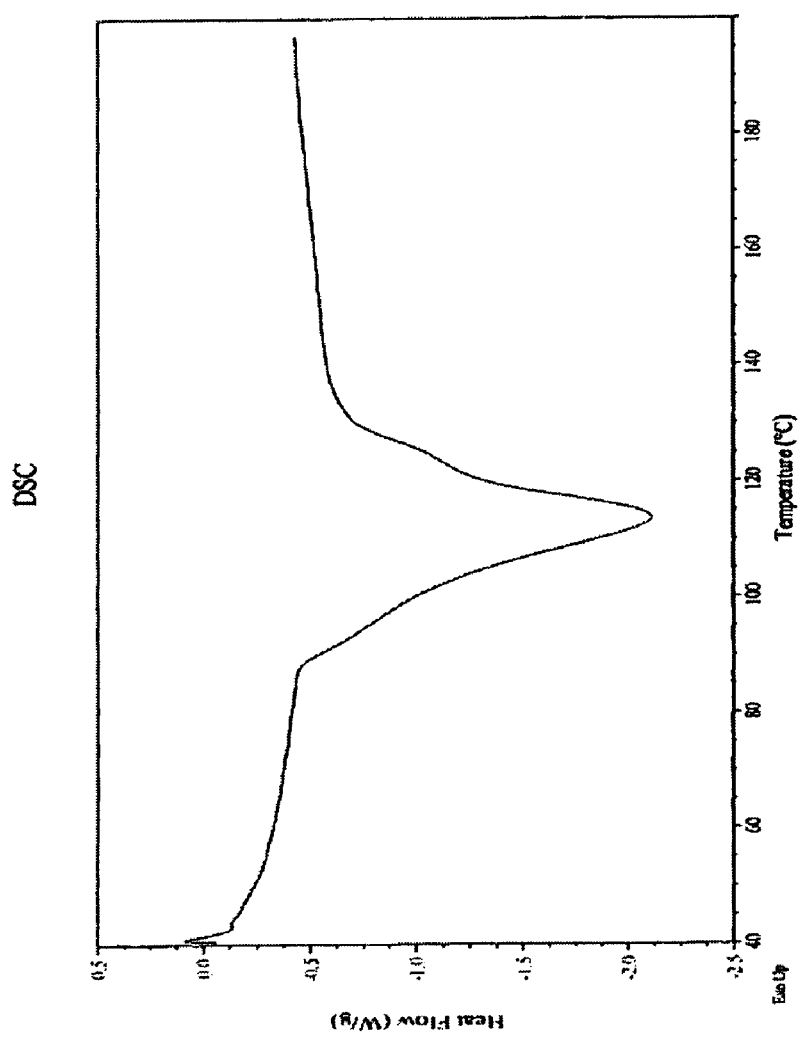
FIG. 2 presents the Differential Scanning Calorimetry (DSC) curve of BIOS-Na monohydrate, prepared as described in Example 1 of U.S. Pat. No. 4,172,896.

FIG. 2 presents the Differential Scanning Calorimetry (DSC) curve obtained for the BIOS-Na monohydrate prepared as above and clearly shows that the obtained BIOS-Na is a monohydrate, exhibiting sharp heat absorption at about 110-120° C.

Figure 3:
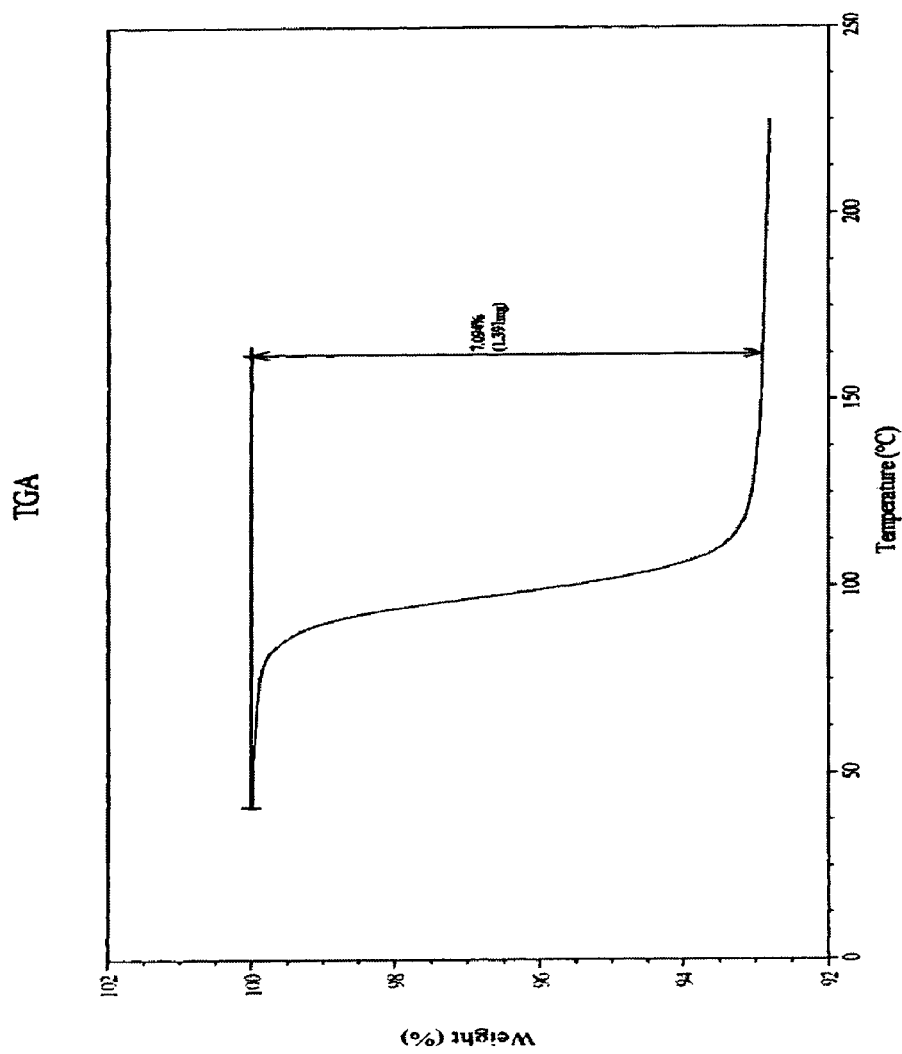
FIG. 3 presents the Thermal Gravimetric Analysis (TGA) thermogram of BIOS-Na monohydrate, prepared as described in Example 1 of U.S. Pat. No. 4,172,896.

FIG. 3 presents the Thermal Gravimetric Analysis (TGA) thermogram obtained for the BIOS-Na monohydrate prepared as above and clearly shows a change in the compound's weight at about 100° C., which corresponds to about 7% water content.

Example 1

Preparation of BIOS-NA$_4$

A solution of ammonium sulfite monohydrate (110 grams, 0.82 mole) in water (1.6 liter) was added to a solution of 3-bromomethyl-1,2-benzisoxazole (100 grams, 0.47 mole) in methanol (1.6 liter) and the mixture was heated, while stirring, at 40-60° C. for 4 hours. The solvents were thereafter removed under reduced pressure and the obtained solid residue was extracted with warm methanol (2.5 liters). The insoluble material was collected by hot filtration and the methanol was removed from the filtrate under reduced pressure. The solid residue was washed with tert-butyl methyl ether and dried on air to obtain BIOS-NH$_4$ (107.5 grams, 0.467 mole, 99% yield).

m.p.=270.2-271.3° C.

The water content of the product, as measured by Karl Fischer (KF) method corresponded to a TGA weight loss step (se, FIG. 7) and was found to be 0.1%.

The crystalline BIOS-NH$_4$ was further characterized by X-Ray Powder Diffraction (XRD), Fourier Transform Infra- Red Spectroscopy (FTIR), Differential Scanning Calorimetry (DSC), Thermal Gravimetric Analysis (GA) and Karl Fischer titration (KF).

FIG. 4 presents the X-Ray Powder Diffraction (XRD) pattern of the BIOS-NH$_4$ and clearly shows that the crystalline BIOS-NH$_4$ is characterized by significant X-Ray Powder Diffraction (XRD) pattern peaks at 2θ values of about 4.8, 9.6, 17.2, 19.3, 24.3, 25.7, 29.5, 29.8, 30.9, 32.6 and 34.2±0.2°.

FIG. 5 presents the FTIR spectrum of the BIOS-NH$_4$ and clearly shows that the crystalline BIOS-NH$_4$ is characterized by absorption peaks at about 3184, 3074, 2924, 2854, 1608, 1515, 1456, 1384, 1262, 1194, 1047, 761, 662 and 579 cm$^{-1}$. The most characteristic FTIR peaks are at about 3184, 3074, 1455, 1194, 1047 and 761 cm$^{-1}$.

FIG. 6 presents the DSC profile of the crystalline BIOS-NH$_4$ and clearly indicates no change in the compound's characteristics.

FIG. 7 presents the TGA thermogram of the crystalline BIOS-NH$_4$ and shows a LOD value of about 0.1% in a temperature range of from 40 to 200° C.

Example 2

Preparation of Zonisamide from BIOS-NH$_4$

A 1.0 liter three-necked flask, equipped with thermometer, mechanical stirrer, Dean-Stark trap and condenser, was charged with crude BIOS-NH$_4$ (50 grams, 0.217 mole) and toluene (520 ml). The resulting suspension was heated to reflux while azeotropic distillation of water was performed, during 2 hours. Then, the mixture was cooled under nitrogen atmosphere to 10° C. and DMF (17 ml, 1.0 molar equivalents) was added to the mixture. Oxalyl chloride (19.9 ml, 0.228 mole, 1.05 molar equivalents) was added dropwise to the mixture at 10-15° C. during 1 hour and the reaction mixture was thereafter heated to 40° C. for 2 hour. Ammonia (gas) (14.8 grams, 4 molar equivalents) was then bubbled into the reaction mixture at 10-18° C. during 2 hours. A precipitate was collected by filtration and slurried in water (200 ml) at ambient temperature for 2 hours. The solid was collected by filtration, washed with water and dried under reduced pressure at 50° C. overnight to obtain crude zonisamide (42.8 grams, 93% yield) having a purity of 99.05%, as determined by HPLC.

Purifying the crude zonisamide was performed by heating a mixture of crude zonisamide (42.8 grams), methanol (410 ml) and water (55 ml) to obtain a solution. The hot mixture was then filtered and methanol (about 180 ml) was distilled from the filtrate. The residual solution was cooled to ambient temperature and was kept at 10-15° C. for 16 hours. The colorless crystals thus obtained were then collected by filtration, washed with a cooled mixture of water and methanol and dried under reduced pressure at 50° C. overnight to obtain zonisamide (34.6 grams, overall yield of 75%) having a purity of 99.95%, as determined by HPLC.

Example 3

Preparation of zonisamide from 1,2-benzisoxazole-3-methanesulfonic acid methyl ester A 250 ml three necked flask, equipped with mechanical stirrer, Dean-Stark trap and condenser, was charged with 1,2-benzisoxazole-3-methanesulfonic acid methyl ester (10 grams, 0.044 mole, obtained from a commercial vendor) and toluene (100 ml). The suspension was heated to reflux while azeotropic distillation of water was performed, during 2 hours. The mixture was thereafter cooled under nitrogen atmosphere to 10° C. and DMF (0.36 ml, 0.0044 mole, 0.1 molar equivalent) was added to the mixture. Oxalyl chloride (4.1 ml, 0.047 mole, 1.07 molar equivalent) was then added drop-wise at 10-15° C. during 30 minutes and the reaction mixture was heated to 40° C. and was kept at this temperature for 4 hours. Ammonia (gas) (3.0 grams, 4 molar equivalents) was then bubbled into the reaction mixture at 10-18° C. during 2 hours and the reaction mixture was kept at ambient temperature overnight. The obtained precipitate was collected by filtration and slurried in 25% ammonium hydroxide (40 ml) at ambient temperature for 2 hours. The obtained solid was collected by filtration, washed with water and dried under reduced pressure at 50° C., overnight to obtain crude zonisamide (7.4 grams, 80.4% yield) having a purity of 98.7%, as determined by HPLC.

Purification of the crude zonisamide was performed by heating a mixture of the crude zonisamide (7.4 grams), methanol (70 ml) and water (10 ml) to obtain a solution, filtering the hot solution and distilling methanol (about 30 ml) from the filtrate. The residual solution was then cooled to ambient temperature and was kept at 10-15° C. overnight to allow crystallization. The obtained colorless crystals were then collected by filtration, washed with a cold mixture of water and methanol and dried under reduced pressure at 50° C. overnight to obtain zonisamide (6.0 grams, 65% overall yield), having a purity of 99.89%, as determined by HPLC.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is

1. A 1,2-benzisoxazole-3-methanesulfonic acid ester of the formula:

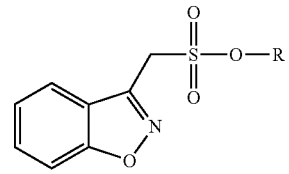

wherein R is selected from alkyl, cycloalkyl, aryl, aralkyl and alkaryl.

2. A process of preparing 1,2-benzisoxazole-3-methanesulfonic acid ammonium salt, the process comprising; providing a first mixture containing 3-bromomethyl-1,2-benzisoxazole and a first alcohol; providing a second mixture containing ammonium sulfite and water; reacting said first mixture and said second mixture to thereby obtain a reaction mixture containing the 1,2-benzisoxazole-3-methanesulfonic acid ammonium salt; and isolating the 1,2-benzisoxazole-3-methanesulfonic acid ammonium salt from said reaction mixture, thereby obtaining the 1,2-benzisoxazole-3-methanesulfonic acid ammonium salt.

3. The process of claim 2, wherein said first alcohol is selected from the group consisting of methanol, ethanol, 1-propanol and 2-propanol.

4. The process of claim 2, wherein said isolating is effected by: removing said first alcohol and said water from said reaction mixture, to thereby provide a residue containing the 1,2-benzisoxazole-3-methanesulfonic acid ammonium salt; dissolving said residue in a second alcohol, to thereby provide a solution containing said 1,2-benzisoxazole-3-methanesulfonic acid ammonium salt and optionally insoluble impurities; filtering said insoluble impurities; and removing said second alcohol.

5. The process of claim 4, wherein said second alcohol is selected from the group consisting of methanol, ethanol, 1-propanol and 2-propanol.

6. A process for preparing zonisamide, the process comprising converting the 1,2-benzisoxazole-3-methanesulfonic acid ester of the formula:

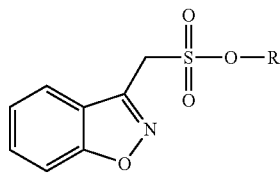

wherein R is selected from alkyl, cycloalkyl, aryl, aralkyl and alkaryl, into zonisamide.

\* \* \* \* \*